United States Patent [19]

Thiele

[11] Patent Number: 4,679,267
[45] Date of Patent: Jul. 14, 1987

[54] RESTRAINING SAFETY HARNESS

[76] Inventor: Edith A. Thiele, 405 W. Haven, New Lenox, Ill. 60451

[21] Appl. No.: 846,204

[22] Filed: Mar. 31, 1986

[51] Int. Cl.⁴ .......................... A47G 9/02; A61F 13/00
[52] U.S. Cl. ........................................... 5/494; 5/496; 128/134
[58] Field of Search .................. 5/424, 494, 496, 498; 128/133, 134

[56] References Cited

U.S. PATENT DOCUMENTS

| | | | |
|---|---|---|---|
| 1,169,607 | 1/1916 | Blenis | 128/134 |
| 2,449,675 | 9/1948 | Schowalter | 128/134 |
| 2,850,746 | 9/1958 | Foehner | 5/494 |
| 2,927,581 | 3/1960 | Queen | 5/424 |
| 3,137,294 | 6/1964 | Robertson | 128/134 |
| 4,143,654 | 3/1979 | Sherman | 128/134 |

Primary Examiner—Gary L. Smith
Assistant Examiner—Michael F. Trettel
Attorney, Agent, or Firm—Charles F. Lind

[57] ABSTRACT

The disclosed safety blanket provides a main generally rectangular panel sized to fit over the bed and substantially cover a person lying thereon. Strap means at the corners (and optionally along the side and/or bottom edges) of the main panel, operate to secure the blanket to the bed frame and over the person lying on the bed. Inner and outer harness panels are provided as part of, or are secured to, the main blanket panel; the inner and outer panels being sized to fit substantially around the chest of the person, and over the shoulders of the person; the inner and outer panels having edges defining openings to receive the person's head and arms; and the inner panels having ends designed to overlap with one another, generally adjacent the back of the person. Velcro hook-loop fasteners on the panel ends allow the ends to be removably secured together, enclosing the harness panels as a continuous loop around the person, operable to hold the person relative to the blanket.

20 Claims, 5 Drawing Figures

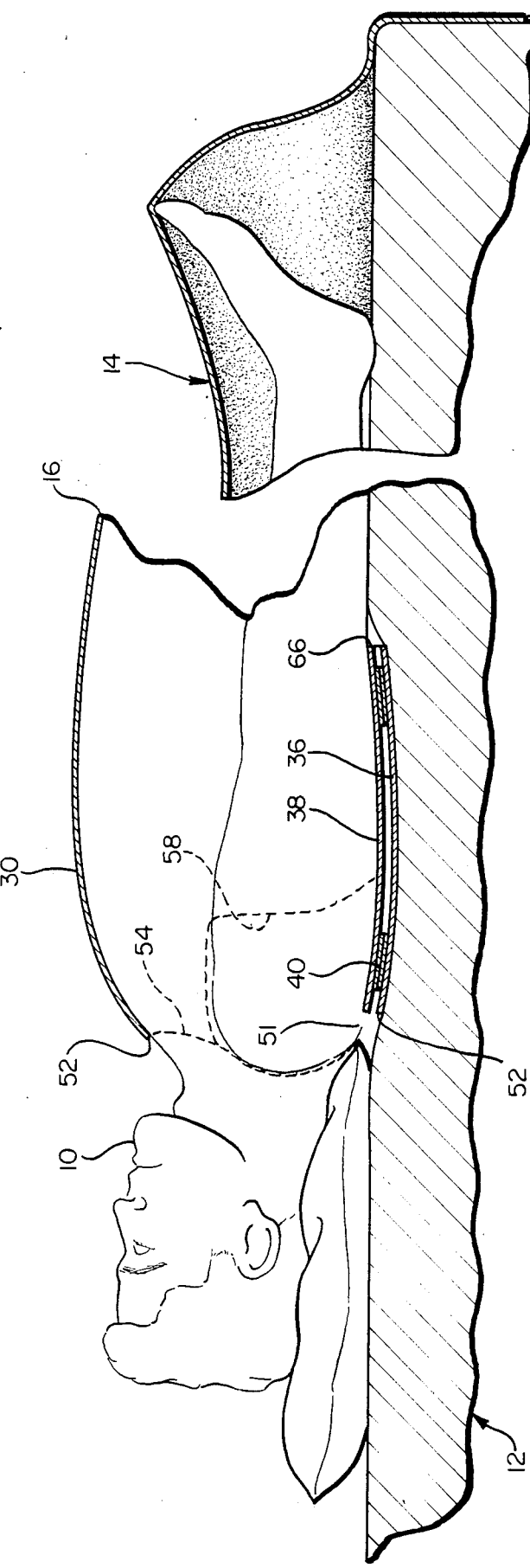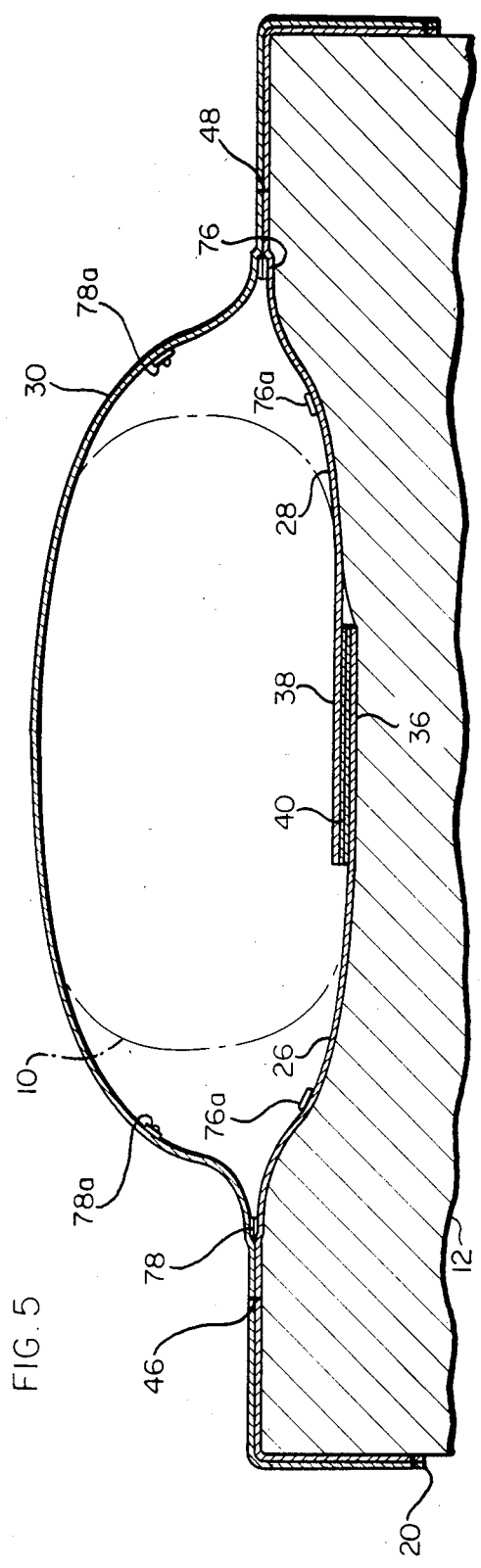

RESTRAINING SAFETY HARNESS

FIELD OF THE INVENTION

This invention relates to a blanket or the like to be extended over a person lying on a bed for covering the person; and to a harness or the like to hold the person in the bed, particularly as might be needed to preclude someone who is physically or mentally incapable of leaving the bed, for his/her own security and safety.

BACKGROUND OF THE INVENTION

In many situations, such as in caring for an older person, either physically or mentally incapable of venturing from the safety and security of his/her bed, it may be necessary to provide a continuous restrain on the person. Of course, depending on the severity of the incapacity, this restrain should also provide for some freedom of movement while safely within the bed, and for dignity of restrain, if possible.

One common restraining device is in the form of an elongated strip that is wrapped around the chest or waist of the person, with one end being fitted through a slot formed in a mid-part of the strip to define a confining loop around the person; and the ends of the strip are then extended under the bed frame and tied together, or are otherwise secured to the bed frame. This looped strip, with the person constrained therein, serves to hold the person in the bed.

Another common restraining device has an elongated strip, somewhat like the looped strip just mentioned, but is larger across it middle and has arm openings formed therein, through which the person's arms are fitted, thereby also defining straps that fit over the person's shoulders, to define a harness; where the extended ends are then wrapped around the back of the person, with one end being fitted through a slot formed in a mid-part of the strip to define the confining loop around the person; and where the ends of the strip are then extended under the bed frame and tied together, or are otherwise secured to the bed frame. This looped harness, with the person constrained therein, also serves to hold the person in the bed.

Drawbacks to the looped strip and/or the looped harness device include the possibility of the person squirming around on the bed, to the degree that upon the person turning in one direction (rolling from lying on the back to lying on the side, for example), the confining loop can be tightened down around the person to the point of causing discomfort. Also the constraining loop can be worked upwardly on the person, to end up around the person's neck, to present the possibility of even choking the person. When the person turns to loosen the loop, and squirms, another drawback is that the restraining loop may loosen to the degree that the person may actually squirm completely out of the loop.

Efforts to avoid these drawbacks, by initially tightening down the constraining loop around the person's waist or chest, work to a degree; but the immediate feeling of being subjected to a greater restrain frequently can backfire, to worsen the situation rather than remmedy it. Thus, the tightened restraining loop commonly makes the active person squirm more, to accererate the possibility of discomfort of, choking by, and/or escape from the tightened constraining loop. On the other hand, a more docile person may be effectively restrained; but even upon that person turning or attempting to turn in the direction to tighten the loop, may tighten the loop even further to provoke discomfort and/or added danger of choking.

Also, as these restrains must both be fitted around the person and then through the strip slot to complete the loop, at times it may be difficult to secure onto the person. Moreover, as the looped device can quite easily become entangled about or tightened on the person, it may also be difficult to take the device off of the person.

An ultimate form of restraining device may be a padded cuff having elongated securing straps. The cuff is secured around the person's wrist or ankle, and then the straps are tied to the underlying bed frame. The device allows movement of the cuff only within the length of the securing strap; which if drawn tightly, can almost totally restrain the wrist or ankle from moving.

The cuff restrain commonly may be used in combination with the above-mentioned restrains, such as to restrain the wrist of someone who may try to remove an IV hook-up, or the like. On severe cases, four such restraining devices may even be used, on both wrist and ankles, such as with the person in a "spread-eagle" configuration, to totally restrain both wrists and ankles from moving beyond the lengths of the straps. However, as this restraining device precludes even the simpliest of personal actions, such as scratching one's nose or wiping one's brow, it should be used only on the most severe cases, or it otherwise may be so effective as a restrain to the point of being undignified and/or even inhumane.

It may also be necessary to provide a blanket having tie-down straps at the corners, whereby the straps may be secured to the underlying bed frame, to serve to keep the person covered. However, such tie-down blankets do not securely and/or safely restrain the person in the bed.

SUMMARY OF THE INVENTION

It is a general object of the present invention to provide a new and improved safety blanket that can easily be secured onto, or taken off of, a person lying on a bed; that is effective to maintain the person covered, regardless of his/her minor squirming and/or kicking about; and that also is effective to prevent the person from gettng out of the bed, while allowing considerable freedom of movement of the person yet constrained under the blanket.

Several general features of this invention are: the harness panels are formed as part of the safety blanket, being suited to be wrapped around the person's chest and back, with free ends that can then be overlapped and secured together, as be Velcro hook-loop fasteners, to hold the person relative to the blanket; the securing means on the harness panel ends normally end up under or on the back side of the person constrained by the blanket, to make it difficult for the person to take off the safety blanket unsupervised; and the harness panels may be adjusted in size to provide a universal blanket suited for restraining people differing from one another over a wide range of sizes.

BRIEF DESCRIPTION OF THE DRAWINGS

Further objects, features and advantages of the present invention will appear from the following description, taken with the accompanying drawings, in which:

FIGS. 4 and 5 are sectional views as seen generally from lines 4—4 and 5—5 of FIG. 1.

DETAILED DESCRIPTION OF AN ILLUSTRATED EMBODIMENT

Figure 1:
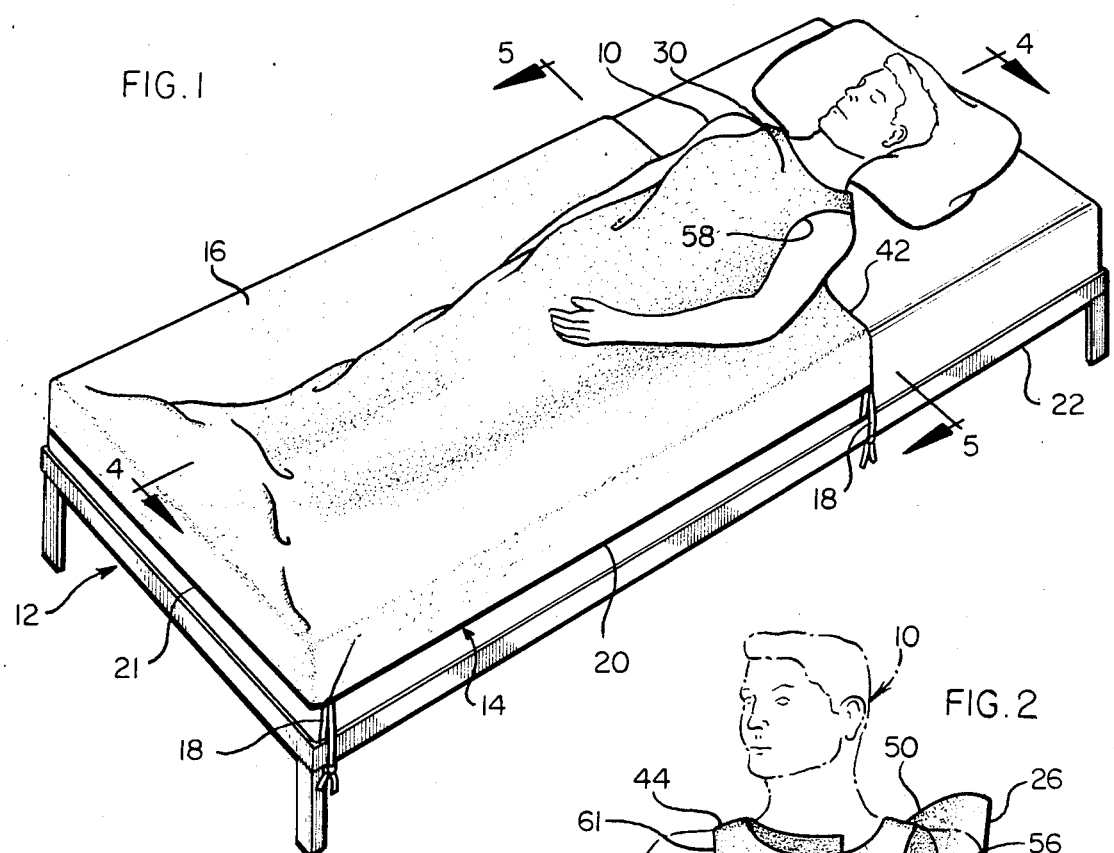
FIG. 1 is a perspective view of the safety blanket shown in operative association with a person lying on a bed.
Figure 2:
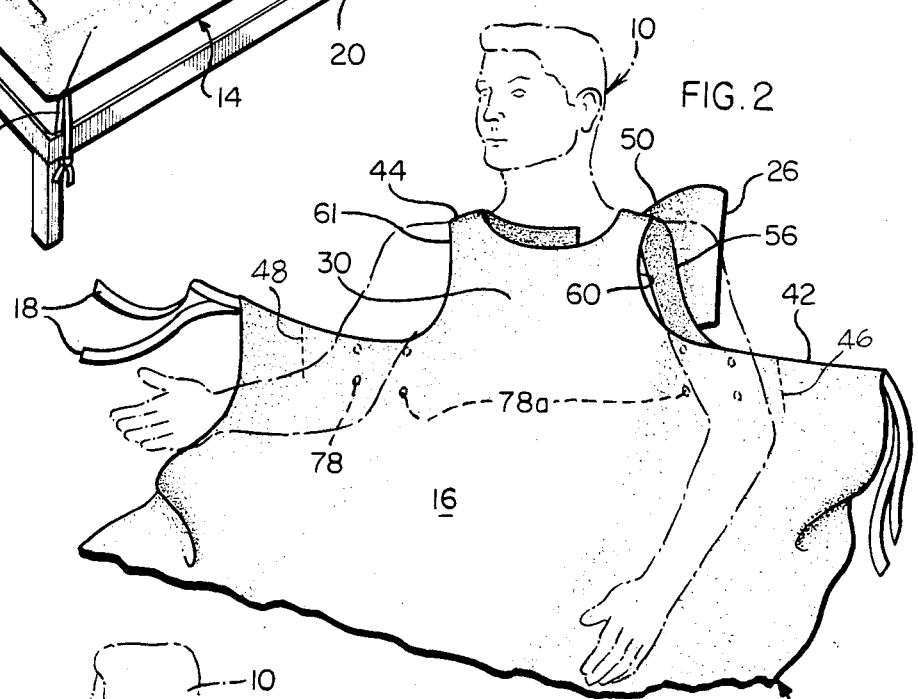
FIG. 2 is a front or outer-side perspective view of the safety blanket, being shown in non secured association with the person.
Figure 3:
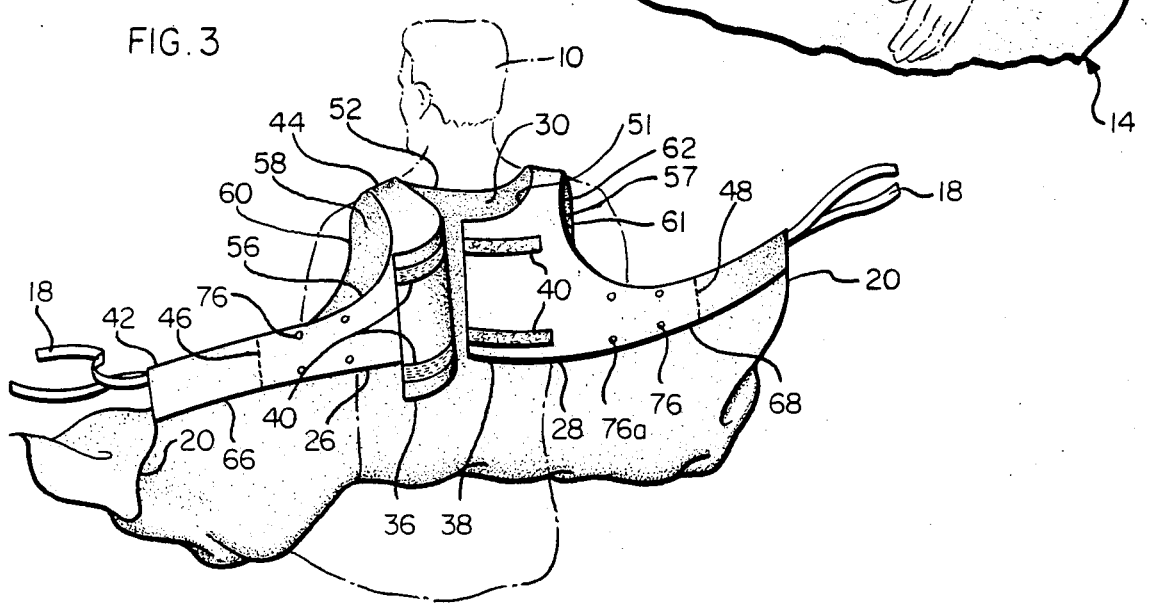
FIG. 3 is a rear or inner-side perspective view of the safety blanket, again being shown in non secured association with the person.

FIG. 1 illustrates a person 10 lying on a bed 12, and a preferred embodiment of the improved safety blanket 14 shown in operative association overlying the person. The blanket 14 has a main generally rectangular panel 16 sized to fit over the bed 12 and substantially cover the person 10 lying thereon. Conventional strap or tie means 18 are provided at the corners of the main panel 16 (and optionally at mid locations along the side and bottom edges 20 and 21 respectively of the blanket 14) operable to secure the blanket to the bed frame 22, and covering the person.

Inner harness panels 26 and 28, and outer harness panel 30 are provided, being secured to or otherwise being a unitary part of the blanket 14. The inner and outer panels 26, 28 and 30 are sized to fit with substantial clearance around the chest of the person 10, and yet have ends 36 and 38 of the inner panels overlap one another. Means 40 are provided for removably securing the overlapped ends 36 and 38 of the inner panels 26 and 28 together; defining then with the harness panels 26, 28 and 30, a continuous loop enclosing the person 10.

A preferred form of the securing means 40 on the ends 36 and 38 of the inner panels 26 and 28 may be in the form of strips of cooperating Velcro hook-loop fasteners, sewn or otherwise secured to the adjacent faces of the panels.

The outer harness panel 30 may be seamed to, or otherwise formed unitary with, the main blanket panel 16, near the top edge 42 and the lateral mid-point thereof. The inner and outer harness panels 26 and 30, and 28 and 30, may be seamed together and/or otherwise may be unitary with one another, in the strap regions at 44 that overlie the person's shoulders. Each inner harness panel 26 and 28 may be secured to the outer harness panel 30 and/or the main blanket panel 16 along spaced seams 46 and 48 laterally and outwardly beyond the person 10.

The edges 50, 51 and 52 of the inner and outer harness panels, define a head opening 54. When the harness panels 26, 28 and 30 are secured around the person, the person's head H fits through the harness head opening 54, to be exposed and free to turn. A typical head opening 54 may be of the order of between 8 and 12 inches diameter.

Typically, the inner and outer panels 26 and 28 will be fitted around the head and neck region of the person, when the panels are open and unsecured; and only when the lapped panel ends are connected will the head opening 54 actually be defined.

The edges 56 and 57, and 60 and 61 of the inner and outer harness panels 26, 28 and 30, define arm openings 58 and 62, respectively. When the harness panels 26, 28 and 30 are secured around the person, the person's arms thus fit through the harness arm openings 58 and 62, to be exposed and free to move about. The arm openings 58 and 62 may be irregular in shape when opened fully, but each may typically be between 10 and 15 inches when the adjacent panels are flat and extended tightly. This provides ample clearance for the arm within the harness arm opening; while the opening yet is not large enough for the person to remove his/her arm from it, when the harness is secured around the person's body.

The bottom edges 66 and 68 of the inner panels 26 and 28, respectively, may be designed to cross the harnessed person in the lower region of the person's rib cage. The inner panels 26 and 28 may overlap with the main panel 16 near its top edge 42 thereof, and these operlapped panels may be sewn together in the regions between the seams 46 and 48, and the adjacent side edges 20 of the blanket. The overlap of inner panels and the main panel 16 may be between 3–6 inches.

The lapped ends 36 and 38 of the inner panels 26 and 28, when secured together, normally are in the region underlying the person 10 lying on the bed 12; and thereby normally are beyond the reach of the secured person's hands. This makes it most difficult for the person to separate the lapped panel ends, by himself/herself, to effect a solo or unsupervised removal of, or escape from the restrainment of, the blanket.

A preferred setting of the harness circumference may be perhaps between 120 and 150 percent that of the person's chest size. This allows quite a bit of freedom for the person to turn from side-to-side, or otherwise move about comfortably in the bed; but nonetheless, holds even a squirming person safely restrained in the bed. For a safety blanket to be of universal size for average size adults, it may be desirable to have the closed harness circumference adjustable between perhaps 35 and 60 inches. This sizing adjustment may be provided, in part, by adjusting the separation between the outboard securement of the inner and main panels; and in part by the degree of overlap of the inner panel ends 36 and 38, when secured together.

Concerning the adjustment of the panel securement separation, the seams 46 and 48 may be sewn and permanent, which represents the largest size of the harness. When the inner panel ends 36 and 38 are exactly overlapped and secured together, with the seams 46 and 48 at a separation of perhaps 27 inches, the harness circumference may then be approximately 54 inches. For smaller sizings of the harness for more universal appeal, one or more sets of releasable securing means, such as snaps 76 and 78, may be secured onto the inner and outer panels, each set being laterally spaced inwardly from the adjacent side seams 46 and 48, or the next adjacent set of snaps, respectively. With perhaps 2 inches separation between the adjacent seams and snaps, 46 and 76, and 48 and 78, with both snaps 76 and 78 secured, the nominal safety harness size will be smaller by approximately 8 inches, to 46 inches circumference; while with another set of snaps 76a and 78a spaced another 2 inches inwardly from the snaps 76 and 78, when these snaps are secured, the safety harness size will be smaller yet by another 8 inches, to approximately 38 inches circumference.

Concerning the adjustment of the harness size by means of the overlap of the panel ends, each panel end may have between 4 and 8 inches width of its hook or loop part of the mating Velcro hook-loop fasteners. In most cases, only about an inch or more of secured overlap is needed in order to retain and hold the safety blanket harness on the person. This provides that the circumference of the secured inner and outer panels may be decreased or increased by perhaps as much as 10–12 inches, merely by shifting the degree of overlap of the inner panel ends 36 and 38.

As the harness, when once secured, has a definite circumference, turning of the secured person within the harness will not tighter it more, to the discomfort or danger of the secured person.

Only one set of releasable securing means or snaps 76 and 78 possibly need be used, at a larger separation of perhaps 4 or 5 inches from the seams 46 and 48; where only one of the snaps might then be secured to provide a moderate reduction of harness size, and where both of the snaps might then be secured to provide a maximum reduction of harness size. With only one of the snaps secured, the harness would be somewhat non-centered relative to the blanket, but the corner ties might then be tightened down defferently to re-center the blanket relative to the bed.

Reducing the size of the harness also reduces the size of the arm openings 58 and 62, although not by the same amount as the harness circumference is reduced. This is so because the opposite ends of each arm opening are defined by the secured or common conections between the inner and outer panels, and a line between these connections is angled relative to the harness circumference adjustment. Also, each upper snap 76a or 78a need not be placed at the upper edge of the adjacent inner and outer panels, which will allow slightly larger arm openings relative to the harness circumference.

The blanket should be made of material that can withstand repeated laundering, while yet have and retain sufficient strength to restrain the harnessed person. This may typically be a cotton, a cotton-synthetic blend, or a synthetic. It may also be advantageous to reinforce the blanket at or across the load regions, such as proximate the tie strap means 18, continuously across the blanket in line with the top edge 42 thereof, or selectively across portions of the inner or outer panels 26, 28 or 30.

While reference has been made only to the term "blanket", the term is meant to include other known bedding items, such as "sheet" or "cover", of related shape and general usage.

OPERATION OF THE INVENTION

The disclosed safety blanket 14 may be easily put on a person 10 lying on a bed 12, by first laying the main panel 16 over the bed and the person, with the open harness inner panels 26 and 28 on opposite sides of the person and aligned somewhat with the person's chest. If possible, the person is then raised to sit up and the person's arms are put through the arm openings 58 and 62, and the inner panels are then wrapped around the back side of the person, to provide the desired circumferential clearance. The panel ends 36 and 38 are then overlapped to set the Velcro fastening means, and close the harness.

If the person is weakened or otherwise cannot sit up, with the person lying or his/her back, and after the person's arm are put through the arm openings 58 and 62, the person is then rolled onto one side, one inner panel is then wrapped around the other side of the person and across and under the person's back, the person is then rolled back onto the one inner panel and to the other side, and the other inner panel is then overlapped and secured to the one inner panel. The chest clearance setting probably will not be too critical for a person in this weakened condition, as determined in part by the degree of overlap of the panel ends 36 and 38.

The person is then laid down, generally on his/her back, and the tie straps 18 of the blanket 14 are secured to the underlying bed frame 22.

The safety blanket 14 can be removed with the reverse steps.

What I claim is:

1. For use with a person lying on a bed having a frame, an improved safety blanket comprising the combination of
   a main generally rectangular panel sized to fit over the bed and substantially cover the person lying thereon,
   one outer and two inner harness panels sized to fit substantially around the chest of the person, and over the shoulders of the person,
   the inner and outer panels having edges defining openings to receive the person's head and arms,
   the outer harness panel being formed as part of and continuous with the main blanket panel, near the top edge and mid-point thereof.
   each inner harness panel being formed as part of and continuous with the outer harness panel, near spaced regions thereof that overlie the shoulders of the person,
   each inner harness panel further being secured to the outer harness panel and the main blanket panel near spaced regions laterally and outwardly beyond the person,
   the inner panels having ends designed to overlap with one another,
   means to removable secure the lapped ends of the inner panels together, enclosing the harness panels as a continuous loop around the person, operable to hold the person relative to the blanket,
   the securing means being in the form of cooperating hook-loop fasteners, allowing the lapped ends of the inner panels to be secured together at adjustable locations, to set the looseness of the harness panels circumferentially when secured on the person,
   the lapped ends of the inner panels, when secured together, normally being in the back region and underlying the person lying on the bed and thereby being beyond the reach of the person's hands, for the person separating the lapped panels, by himself-/herself, for the unsupervised removal from the restrainment of the blanket,
   the regions of securement between each inner harness panel and the outer harness panel and the main blanket panel being spaced apart, when the adjacent panels are flat and extended tightly, between 15 and 25 inches,
   additional releasible securing means secured onto the inner and outer harness panels, being laterally spaced inwardly from the adjacent region of securement of each inner harness panel to the outer harness panel and the main blanket panel, and when selectively secured together providing additional sizing adjustment of the harness, and
   means at the corners of the main panel operable to secure the blanket to the bed frame and over the person lying on the bed.

2. An improved safety blanket combination according to claim 1, wherein the adjustable overlap of the inner panels as secured, and the additional releasible securing means, provide circumferential adjustment of size and looseness of the harness panels to between 120 and 150 percent of the person's chest, when secured on the person.

3. An improved safety blanket combination according to claim 1, wherein the inner panel ends each have between 4 and 8 inches width of the mating hook-loop fasteners.

4. An improved safety blanket combination according to claim 1, wherein the inner and outer panel edges only define the head opening when the lapped panel ends are secured together, the inner panels being normally separate when the harness is open and the panels are unsecured and being fitted around the head and neck region of the person, and the head opening being of the order of between 8 and 12 inches across.

5. An improved safety blanket combination according to claim 1, wherein the panel edges defining the arm openings are concave in shape when the adjacent panels are laid flat together and extended tightly, and wherein the arm openings are between 10 and 15 inches across as the panels are so laid.

6. An improved safety blanket combination according to claim 1, wherein the panels are made of a cotton-synthetic blend that can withstand repeated laundering, while yet have and retain sufficient strength to restrain the harnessed person.

7. For use with a person lying on a bed having a frame, an improved safety blanket comprising the combination of
 a main generally rectangular panel sized to fit over the bed and substantially cover the person lying thereon,
 one outer and two inner harness panels sized to fit substantially around the chest of the person, and over the shoulders of the person,
 the inner and outer panels having edges defining openings to receive the person's head and arms,
 the outer harness panel being formed as part of and continuous with the main blanket panel, near the top edge and mid-point thereof,
 each inner harness panel being formed as part of and continuous with the outer harness panel, near spaced regions thereof that overlie the shoulders of the person,
 each inner harness panel further being secured to the outer harness panel and the main blanket panel near spaced regions laterally and outwardly beyond the person,
 the regions of securement being spaced apart, when the adjacent panels are flat and extended tightly, between 15 and 25 inches,
 the inner panels having ends designed to overlap with one another,
 means to removably secure the lapped ends of the inner panels together, enclosing the harness panels as a continuous loop around the person, operable to hold the person relative to the blanket,
 the securing means being in the form of cooperating hook-loop fasteners, allowing the lapped ends of the inner panels to be secured together at adjustable locations, to set the circumferential harness looseness even when secured on the person,
 the lapped ends of the inner panels, when secured together, normally being in the back region and underlying the person lying on the bed and thereby being beyond the reach of the person's hands, for the person separating the lapped panels, by himself/herself, for the unsupervised removal of the blanket, and
 the bottom edges of the inner panels being designed to cross the harnessed person in the lower region of the person's rib cage, and such inner panels overlapping with the main panel near its top edge thereof, and the overlapped inner and outer panels being secured together outwardly beyond said earlier mentioned regions of securement between each inner and main panels, and
 means at the corners of the main panel operable to secure the blanket to the bed frame and over the person lying on the bed.

8. An improved safety blanket combination according to claim 7, wherein the adjustable overlap of the inner panels as secured provides circumferential adjustment of size and looseness of the harness panels up to 150 percent of the person's chest, when secured on the person.

9. An improved safety blanket combination according to claim 7, wherein the inner panel ends each have between 4 and 8 inches width of the mating hook-loop fasteners.

10. For use in restraining a person relative to a frame, an improved safety harness comprising the combination of
 a pair of inner harness panels and an outer harness panel sized to fit substantially around the chest of the person, and over the shoulders of the person,
 the inner and outer panels, when laid flat together and extended tightly, having edges defining openings to receive the person's head and arms,
 the inner panels being continuous respectively with the outer panel, near spaced regions thereof that overlie the shoulders of the person, and the panel edges defining the head opening being concave upwardly between these spaced regions,
 the panel edges defining the arm openings being concave sidewardly, respectively away from the spaced panel regions that overlie the person's shoulders,
 the inner panels having ends designed to overlap with one another, and being separate when the inner panels are being fitted around the head and neck region of the person,
 means to removably secure the overlapped ends of the inner panels together, enclosing the harness panels continuously around the person,
 the securing means being in the form of cooperating hook-loop fasteners, allowing the overlapped ends of the inner panels to be secured together at adjustable locations, to set the size and looseness of the harness panels circumferentially when secured around the person,
 the overlapped ends of the inner panels, when secured together, normally being in the back region of the person and beyond the reach of the person's hands, for the person separating the panels, by himself/herself, for the unsupervised removal from the secured harness panels,
 each inner panel further being secured to the outer panel near a sideward region laterally and outwardly beyond the person, and
 means to secure the inner and outer panels, from the sideward locations as secured together laterally and outwardly beyond the person, relative to the frame.

11. An improved safety harness combination according to claim 10, further including additional releasable securing means located on the inner and outer harness panels, laterally spaced inwardly from the adjacent region of securement of each inner harness panel to the outer harness panel, and providing additional adjustment of the size and looseness of the harness panels circumferentially when secured around the person.

12. An improved safety harness combination according to claim 11, wherein the adjustable overlap of the inner panels as secured, and the additional releasible securing means, provide circumferential adjustment of size and looseness of the harness panels to between 120 and 150 percent of the person's chest, when secured on the person.

13. An improved safety harness combination according to claim 12, wherein bottom edges of the inner panels are designed to cross the harnessed person in the lower region of the person's rib cage.

14. An improved safety harness combination according to claim 13, wherein the inner panel ends each have between 4 and 8 inches width of the mating hook-loop fasteners, and wherein the arm openings are between 10 and 15 inches across as the panels are laid flat.

15. An improved safety harness combination according to claim 13, wherein the regions of securement are spaced apart, when the adjacent panels are flat and extended tightly, between 15 and 25 inches.

16. An improved safety harness combination according to claim 10, wherein the inner panel ends each have between 4 and 8 inches width of the mating hook-loop fasteners.

17. An improved safety harness combination according to claim 10, wherein the arm openings are between 10 and 15 inches across as the panels are laid flat and extended tightly.

18. An improved safety harness combination according to claim 10, wherein the regions of securement are spaced apart, when the adjacent panels are flat and extended tightly, between 15 and 25 inches.

19. An improved safety harness combination according to claim 10, wherein bottom edges of the inner panels are designed to cross the harnessed person in the lower region of the person's rib cage.

20. An improved safety harness combination according to claim 10, wherein the panels are made of a cotton-synthetic blend that can withstand repeated laundering, while yet have and retain sufficient strength to restrain the harnessed person.

* * * * *